United States Patent [19]

Iwabuchi et al.

[11] Patent Number: 4,517,175

[45] Date of Patent: May 14, 1985

[54] HAIR COSMETICS

[75] Inventors: Hidetoshi Iwabuchi, Sakura; Takeo Okumura, Funabashi, both of Japan

[73] Assignee: Kao Corporation, Tokyo, Japan

[21] Appl. No.: 497,410

[22] Filed: May 23, 1983

[30] Foreign Application Priority Data

Jun. 7, 1982 [JP] Japan .................. 57-96343

[51] Int. Cl.³ ............ A61K 7/06; A61K 37/00; A45D 7/00

[52] U.S. Cl. .......................... 424/70; 424/71; 424/47; 132/7; 8/405; 514/456; 514/801

[58] Field of Search .............. 424/70, 71, 177, 195, 424/283; 132/7; 8/405

[56] References Cited

U.S. PATENT DOCUMENTS

| | | | |
|---|---|---|---|
| 3,957,065 | 5/1976 | Busch et al. | 424/71 X |
| 4,003,999 | 1/1977 | Lybrand et al. | 424/195 |
| 4,186,188 | 1/1980 | Gumprecht et al. | 424/70 |
| 4,439,417 | 3/1984 | Matsunaga et al. | 424/71 X |
| 4,460,566 | 7/1984 | Abe et al. | 424/71 X |
| 4,465,664 | 8/1984 | Matsunaga | 424/71 |

OTHER PUBLICATIONS

Chem. Abs. 91: 145874b (1979).

Primary Examiner—Sidney Marantz
Assistant Examiner—Shawn P. Foley
Attorney, Agent, or Firm—Oblon, Fisher, Spivak, McClelland & Maier

[57] ABSTRACT

Disclosed herein is a hair cosmetic comprising flavanol derivatives. Also disclosed a hair cosmetic comprising flavanol derivatives and peptide compounds. A hair cosmetic comprising flavanol derivatives can impart excellent hair style formability and retentivity and an appropriate degree of smoothness or softness to the hair. Peptide compounds synergistically improve the above performance when used in combination with the flavanol derivatives.

10 Claims, No Drawings

HAIR COSMETICS

BACKGROUND OF THE INVENTION (i) Field of the Invention:

This invention relates to hair cosmetics and more particularly, to hair cosmetics of the type which comprise flavanol derivatives by which they can impart to the hair a suitable degree of style retentivity and good touch or texture with easy combing performance.

(ii) Description of the Prior Art:

Hair style is one of the most important factors in beauty art and a variety of beauty treatments are effected thereon. For instance, techniques for imparting a suitable degree of wave to the hair by the use of hair cosmetics include so-called permanent treatments by permanent wave set and transient treatments such as by set lotion, hair spray and the like. These treatments are used to dress the hair. However, treatments by perm have a possibility of considerably impairing the hair to a state of showing little progress toward recovery. Treatments such as with set lotion, hair spray and the like merely set the hair transiently, with a drawback in that set hair readily loses its shape when exposed to moisture. Both types of treatments are not satisfactory. Additionally, these treatments have the tendency of rendering the hair hard and are not satisfactory with respect to the touch of the hair.

For the purpose of removing stain deposited on the hair, shampoos are used, but commercially available shampoos wash away, in addition to the stain, oils necessary for the hair, leading to unfavorable phenomena such as split ends, broken hairs and the like upon brushing of the hair. In order to overcome this disadvantage, hair rinses, preshampoos and the like are employed, some of which are compounded with oils and fats, rendering the hair sticky.

SUMMARY OF THE INVENTION

In order to obtain hair cosmetics with excellent properties, we have made extensive studies on their ingredients and found that when flavanol derivatives are compounded in hair cosmetics such as shampoos, rinses, set lotions, hair sprays and the like, excellent hair style formability and retentivity and an appropriate degree of smoothness or softness can be imparted to the hair which permits easy combing of the hair.

Furthermore, it was also found that the performance of the above hair cosmetics can synergistically be improved when they are used in combination with peptide compounds such as keratin, collagen, silk and the like.

Accordingly, the present invention comprehends within the scope thereof a first embodiment which provides a hair cosmetic comprising flavanol derivatives and a second embodiment which provides a hair cosmetic comprising flavanol derivatives and peptide compounds.

DETAILED DESCRIPTION OF THE INVENTION AND PREFERRED EMBODIMENTS

Flavanol derivatives useful in the present invention are polyoxy derivatives (catechins) of 3- and 4-oxyflavanol. Typical examples of the compounds are shown below.

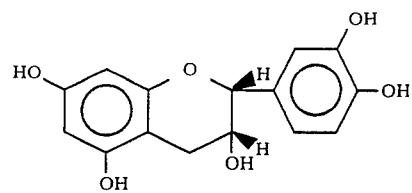

Epicatechin

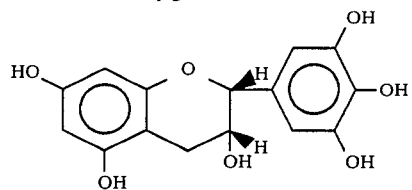

Epigallocatechin

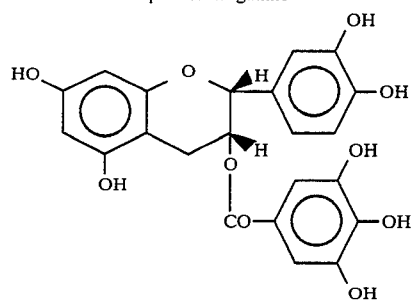

Epicatechin gallate

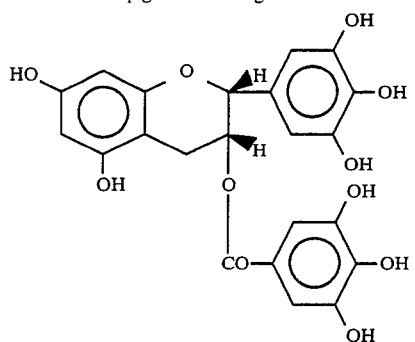

Epigallocatechin gallate

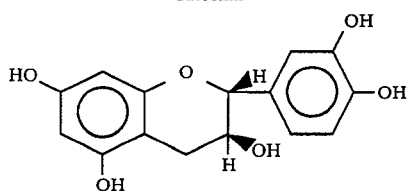

Catechin

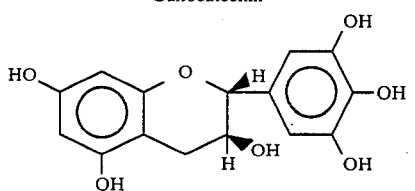

Gallocatechin

Gallocatechin gallate

-continued

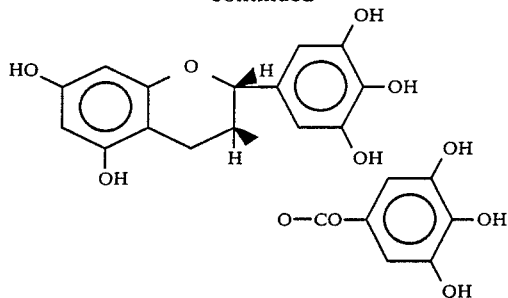

Catechin gallate

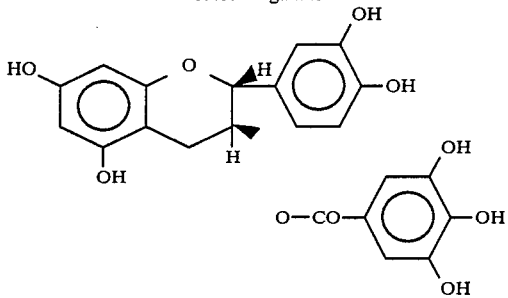

These flavanol derivatives may be of any types including extracts from natural products, purified products isolated from extracts, and synthetic products.

Examples of extracts from natural products include those from tea.

Various flavanol derivatives are present in tea leaves, typical ones of which are epicatechin, epicatechin gallate, epigallocatechin, epigallocatechin gallate, catechin, gallocatechin and the like. The total content of these derivatives in tea leaves amounts to as high as 15–20%. Portions to be used for extraction are not critically limited and include leaves, stems and the like. Any tea leaves can be used including black tea which is a fermented tea, oolong tea which is a semi-fermented tea, and green tea which is a non-fermented tea. Of these, green tea has the highest content of flavanol derivatives and is preferably used. All the types of green tea such as gyokuro tea (i.e. supreme tea obtained from sun shaded cultivation), ground tea, parched tea, coarse tea, roasted tea and the like, being obtained from different culture conditions, treatments of tea leaves, can be used.

Extracts from natural sources are obtained by extraction with one or more solvents including lower alcohols such as methanol, ethanol and the like; polar organic solvents such as acetone, ethyl ether, ethyl acetate and the like; and non-polar solvents and water. The extract may be effected at a normal temperature or under heating conditions. If necessary, the solvent used is distilled off to obtain an extract for subsequent use. The extraction may be effected by any known techniques. In order to increase an extraction effect, it is preferable to use dry powder of tea and immerse it in solvents for extraction.

The resulting flavanol derivatives should be incorporated in hair cosmetic in an amount of at least 0.0001 wt. % (hereinafter referred to simply as %) in total. The upper limit of the amount of flavanol derivatives is not critical but even if they are added in amounts larger than 1%, no further improvement in performance of hair cosmetics can be expected. Thus, amounts larger than 1% are not favorable in economy. Accordingly, flavanol derivatives are preferably used in amounts of 0.0005–0.1%, most preferably 0.001–0.05%, of hair cosmetics.

Preferable peptide compounds used in the second embodiment of the present invention include collagen, keratin, silk and the like.

(1) Collagen

Collagen used in this invention is not limited to any specific types but preferable materials include gelatin, glue, collagen fiber, collagen film and the like. These materials may be used as fine powder or a high—low molecular weight decomposition product obtained by hydrolysis. When a hydrolyzate is used, its molecular weight is generally in the range of 100–300,000, preferably 350–30,000. Collagen is obtained from bone, connective tissue and the like of animals. For instance, those collagens obtained from materials such as true skin, intine, tendon, cartilage and the like can be all used for the purpose of the invention. Commercially available collagen products are Promois (Seiwa Chem. Co., Ltd.), New Trillan (Glueno Co., Ltd.), Protein (Kloda Co., Ltd.) and the like.

(2) Keratin

The term "keratin" used herein means keratin per se and derivatives thereof.

Examples of keratin include animal hairs, human hair, feathers, nails, horns, hooves, scales and the like. These may be used in the form of fine powder, and preferably, decomposition derivatives of these materials are used. Preferable keratin materials are wool, human hair and feathers.

Decomposition derivatives of keratin are hydrolyzates, oxidation decomposition products and —SH group-modified compounds of reduction decomposition products. Hydrolysis, oxidation and reduction and subsequent modification reactions can be appropriately used in combination. Examples of hydrolytic agents include acids such as hydrochloric acid, sulfuric acid, phosphoric acid and the like, bases such as sodium hydroxide, sodium carbonate and the like, and enzymes such as protease. Oxidation and reduction reactions are carried out by known techniques. By the reduction reaction disulfide bonds are leaved and thiol groups (—SH) are formed. The thiol groups can be modified by known methods into the following groups:

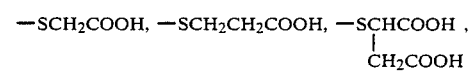

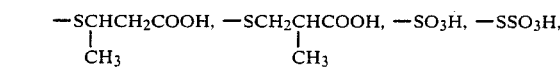

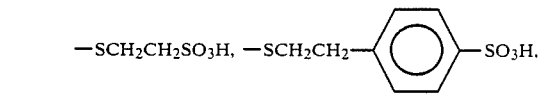

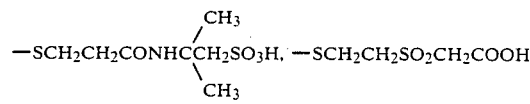

and the like. Of these, modification into the groups of

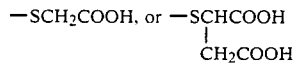

are preferable.

Chemical modification of the thiol group can be effected by methods known per se, for example, based on the methods described in "Textile Progress" Vol. 7, page 1 (1975) by N. H. Leon, "Organic Sulfur Compounds" (1968) written by Shigeru Ooae and published by Kagaku Dojin, and "Kobunshi Jikken Koza" Vol. 12 (1957), written by Masami Oku and published by Kyoritsu Shuppan K. K.

These decomposition products of keratin and derivatives thereof have a molecular weight of 100–100,000, preferably 350–30,000.

(3) Silk

Silk, i.e., silk fiber, may be used after fine powdering of silk itself or its pickled product. Preferably, products obtained by acid, alkali or enzyme hydrolysis are used.

Silk fiber can be hydrolyzed either by an acid such as hydrochloric acid, sulfuric acid, phosphoric acid or the like, or by an alkali such as sodium hydroxide, sodium carbonate or the like with or without use of an enzyme in combination. The hydrolyzate has a molecular weight of 100–100,000, preferably 350–30,000.

The amount of the peptide compound is in the range of 0.01–10%, preferably 0.05–3%, of hair cosmetics.

The term "hair cosmetic(s)" used herein is intended to mean all cosmetics applied to the hair. For example, there are included hair treatments such as preshampoo treatment, shampoo, hair rinse, after shampoo, conditioner, hair conditioner, set lotion, blow styling lotion, hair spray, hair dye, bleach, permanent wave first agent, permanent wave second agent, hair liquid, hair tonic and the like.

Accordingly, the hair cosmetics of the present invention are prepared by admixing, with the above-described essential ingredients, known ingredients which vary depending on the type of hair cosmetic. The hair cosmetics of the invention may have any preparation forms, depending on the purpose, such as of an aqueous solution, ethanol solution, emulsion, suspension, gel, solid, aerosol, powder and the like.

Typical procedures of preparing hair cosmetics according to the invention are described hereinbelow.

(1) Shampoo

According to the usual procedure, one or more of anionic surface active agents and the essential ingredients used in the present invention are admixed with ingredients of known shampoo composition to prepare shampoos.

Preferable anionic surface active agents which are a substrate of shampoo are as follows.

① Linear or branched alkylbenzenesulfonates having an alkyl group containing 10–16 carbon atoms on average.

② Polyoxyalkylenealkylsulfates having a linear or branched alkyl group having 8–20 carbon atoms on average, with 0.5–8 moles, on average, of ethylene oxide and/or propylene oxide being added in one molecule.

③ Alkylsulfates having an alkyl group having 10–20 carbon atoms on average.

④ Olefinsulfonates having 10–20 carbon atoms in one molecule thereof on average.

⑤ Alkanesulfonates having 10–20 carbon atoms in one molecule thereof on average.

⑥ Alkylethoxycarboxylates having an alkyl group with 10–20 carbon atoms on average and having 0.5–8 moles, on average, of ethylene oxide added in one molecule thereof.

⑦ Succinic acid derivatives represented by the formula,

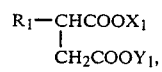

in which $R_1$ represents an alkyl or alkenyl group having 6–20 carbon atoms, and $X_1$ and $Y_1$ independently represent an ion.

Counter ions of these anionic surface active agents include alkali metal ions such as sodium, potassium and the like; alkaline earth metal ions such as calcium, magnesium and the like; ammonium ion, alkanolamines having 1–3 alkanol groups each having 2 or 3 carbon atoms (such as, for example, monoethanolamine, diethanolamine, triethanolamine, triisopropanolamine and the like), and the like.

Of these anionic surface active agents, most preferable agents are linear or branched alkylsulfates having an average number of carbon atoms of 10–16, polyoxyethylene alkylsulfates (an average number of addition moles of 0.5–8) whose alkyl group has an average number of carbon atoms of 8–20, and olefinsulfonates having an average number of carbon atoms of 10–16.

In the shampoo according to the present invention, the amount of an anionic surface active agent is in the range of 5–30 wt. % (hereinafter referred to simply as %), preferably 10–25%.

Other ingredients may include, within ranges of amounts not impeding the effect of the invention, amphoteric surface active agents, nonionic surface active agents, cationic surface active agents, solubilizers such as propylene glycol, glycerine, urea and the like; viscosity adjusters such as ethyl alcohol, isopropyl alcohol, hydroxyethyl cellulose, methyl cellulose, higher alcohols and the like; perfumes, colorants, UV absorbers, antioxidants, preservatives, pearling agents, lotionizing agent and the like. These ingredients can be added as required.

The thus obtained shampoo of the invention is excellent in hair conditioning and in washing effects. Also, it is less irritative than conventional shampooes when brought into touch with eye by mistake and gives a rather mild influence on the conjuctiva and the iris.

(2) Hair Rinse, Hair Conditioner, Hair Treatment

The essential ingredient or ingredients are dissolved or dispersed in a suitable solvent such as water, ethanol, glycerine, ethylene glycol, propylene glycol, 1,3-propanediol, isopropanol, polyethylene glycol or the like to obtain an intended product.

These hair cosmetics such as a hair rinse of the invention may be further admixed with known ingredients ordinarily used in these compositions. In particular, it is preferable to add a surface active agent selected from cationic surface active agents, anionic active agents, noninic active agents and amphoteric active agents. Of these, cationic surface active agents are most preferable.

Examples of these surface active agents are as follows.

(a) Anionic Surface Active Agents

① Linear or branched alkylbenzenesulfonates having an alkyl group having 10–16 carbon atoms on average.
② Alkyl- or alkenylethoxysulfates having a linear or branched alkyl or alkenyl group having 8–20 carbon atoms on average and having 0.5–8 moles, on average, of ethylene oxide added in one molecule thereof.
③ Alkyl- or alkenylsulfates having an alkyl or alkenyl group having 10–20 carbon atoms on average.
④ Olefinsulfonates having, on average, 10–20 carbon atoms in one molecule thereof.
⑤ Alkanesulfonates having 10–20 carbon atoms in one molecule thereof on average.
⑥ Salts of saturated or unsaturated fatty acids having, on average, 10–20 carbon atoms in one molecule thereof.
⑦ Alkyl- or alkenylethoxycarboxylates having an alkyl or alkenyl group having 10–20 carbon atoms (preferably 12–16 carbon atoms) on average and having 0.5–8 moles, on average, of ethylene oxide added in one molecule thereof.
⑧ Salts or esters of α-sulfo fatty acids represented by the following general formula:

$$R_2CHCO_2Y_2$$
$$|$$
$$SO_3M_1$$

in which $Y_2$ represents an alkyl group having 1–3 carbon atoms or a counter ion, $M_1$ represents a counter ion, and $R_2$ represents an alkyl or alkenyl group having 10–20 carbon atoms (preferably 12–16 carbon atoms).

Counter ions of the anionic active agents include alkali metal ions such as sodium, potassium and the like, alkaline earth metal ions such as calcium, magnesium and the like, ammonium ion, and alkanolamines having 1–3 alkanol groups having 2 or 3 carbon atoms (e.g., monoethanolamine, diethanolamine, triethanolamine, triisopropanolamine and the like). .

(b) Nonionic Surface Active Agents
① Polyoxyethylene alkyl or alkenyl ethers having primary or secondary alkyl or alkenyl groups each having 8–20 carbon atoms on average and having 3–12 moles of ethylene oxide added.
② Polyoxyethylene alkylphenyl ethers having an alkyl group having 8–12 carbon atoms on average and having 3–12 moles of ethylene oxide added thereto.
③ Higher fatty acid alkanolamides or alkyleneoxide adducts thereof represented by the following formula:

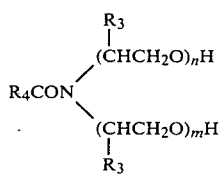

in which $R_3$ represents H or $CH_3$, $R_4$ represents an alkyl or alkenyl group having 10–20 carbon atoms, n is an integer of 1–3, and m is an integer of 0–3.

(c) Amphoteric Surface Active Agents
① Alkylamineoxides represented by the following general formula:

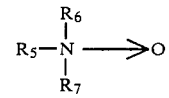

in which $R_5$ represents an alkyl or alkenyl group having 10–20 carbon atoms, and $R_6$ and $R_7$ independently represent an alkyl group having 1–3 carbon atoms and may be the same or different.

Oxides of the above formula in which $R_5$ represents an alkyl or alkenyl group having 12–16 carbon atoms and $R_6$ and $R_7$ independently represent methyl group are preferable.

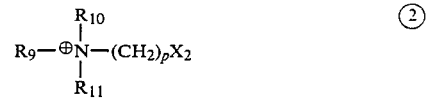

in which $R_9$ represents an alkyl or alkenyl group having 10–20 carbon atoms, $R_{10}$ and $R_{11}$ independently represent an alkyl group having 1–4 carbon atoms, p is an integer of 1–3, and $X_2$ represents a $COO^\ominus$ or $-SO_3^\ominus$ group.

Compounds of the above formula in which $R_9$ represents an alkyl or alkenyl group having 12–16 carbon atoms, $R_{10}$ and $R_{11}$ independently represent a methyl group, and p is a value of 3 are preferable.

③ Imidazoline compounds represented by the following general formula:

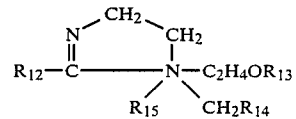

in which $R_{12}$ represents a fatty acid rsidue having an average number of carbon atoms of 10–20, $R_{13}$ represents hydrogen, Na or $CH_2COOMe$ (Me: H, Na or an organic base), $R_{14}$ represents COOMe, $CH_2COOMe$ or

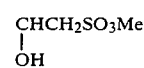

(wherein Me has the same meaning as defined above), and $R_{15}$ represents a hydroxyl group, acidic salt, anionic surface active sulfate or sulfation product. In the formula, $R_{12}$ is preferably a fatty acid residue having 12–16 carbon atoms.

(d) Cationic Surface Active Agents
Cationic surface active agents useful in the present invention are not critically limited and all agents which can be utilized in hair rinse can be used in the practice of the invention. Preferable agents are quaternary ammonium salts represented by the following formula (1):

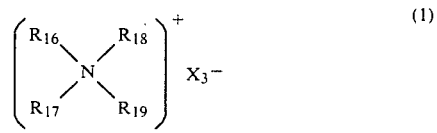

in which one or two of $R_{16}$, $R_{17}$, $R_{18}$ and $R_{19}$ independently represent a long-chain alkyl or long-chain hydroxyalkyl group having 8–20 carbon atoms and the others independently represent an alkyl or hydroxyalkyl group having 1–3 carbon atoms or a benzyl group, and $X_3$ represents a halogen atom or an alkylsulfate having 1–2 carbon atoms. Specific examples of these salts include distearyldimethylammonium chloride, stearyltrimethylammonium methosulfate, stearyltrimethylammonium chloride, stearyldimethylbenzylammonium chloride, lauryldiethylbenxylammonium chloride, lauryltrimethylammonium bromide, distearylmethylhydroxymethyl chloride, cetyltrimethylammonium chloride and the like.

These surface active agents can produce good results when used in an amount of 0.01–10%, preferably 0.5–5%, of hair rinse compositions.

The hair rinse of the invention may further include optional ingredients, i.e., hydrocarbons such as liquid paraffin, vaseline, solid paraffin and the like; esters such as isopropyl myristate; lanolin derivatives such as lanolin, purified lanolin, lanolin fatty acids and the like; silicone derivatives such as dimethylpolysiloxane, methylphenyl polysiloxane, organo-modified polysiloxanes and the like; polyethylene glycol, polypropylene glycol or its polymer; oils such as polyoxyalkylene alkyl ethers, polyoxyalkylene alkyl ether phosphates and the like; polymeric materials such as hydroxyethyl cellulose, hydroxypropyl cellulose, hydroxypropyl methyl cellulose, methyl cellulose, cationized cellulose, cationized polymers and the like; bactericides, preservatives, perfumes, colorants and the like. These ingredients may be added appropriately as desired.

(3) Hair Set Lotions (Set Lotion, Hair Spray, etc.)

Essential ingredient or ingredients of the invention are dissolved as usual in polar solvents such as water, ethyl alcohol, propyl alcohol and the like to obtain lotions. As a matter of course, polymeric compounds which are ordinarily used in conventional hair set lotions can be admixed. Examples of these polymeric compounds are as follows.

(a) Polyvinylpyrrolidone polymeric compounds

Examples of these compounds include polyvinylpyrrolidone, vinylpyrrolidone and vinyl acetate copolymer, and copolymers of vinylpyrrolidone, vinyl acetate and alkylaminoacrylates. Commercially available products include Luviskol K, Luviskol VA and Luviflex D410I (Yuka Burdische Co., Ltd.), PVPK, PVP/VA, E-735 (GAF Co., Ltd.) and the like.

(b) Acidic vinyl ether polymeric compounds

Mentioned as such compounds are lower alkyl half esters of copolymer of methyl vinyl ether and maleic anhydride. Commercially available products include Gantrez ES-225, ES-335 (GAF Co., Ltd.), and the like.

(c) Acidic polyvinyl acetate polymeric compounds

As typical compounds, there are mentioned a copolymer of vinyl acetate and crotonic acid, and the like. Commercially available products include Resin 28-1310 (National Starch Co., Ltd.), Luviset CE5055 (Yuka Burdische Co., Ltd.), and the like.

(d) Acidic acrylic polymeric compounds

Examples of these compounds include copolymers of acrylic acid and/or methacrylic acid and alkyl acrylates and/or alkyl methacrylates, and copolymers of acrylic acid, alkyl acrylate and N-alkylacrylamides. Typical commercial products are Plascize (Gooh Chem. Co., Ltd.), Ultra Hold 8 (Ciba-Geigy A.G.), and the like.

(e) Amphoteric acrylic polymeric compounds

Examples of these compounds are those which are obtained by copolymerizing dialkylaminoethyl methacrylates, dialkylaminoethyl acrylates, diacetone acrylamide, etc. and acrylic acid, methacrylic acid, alkyl acrylates, alkyl methacrylates, etc., followed by amphoterizing with acetyl halide. Commercial products include Yukaformer AM-TS (Mitsubishi Yuka Co., Ltd.).

The hair set lotions of the invention may further comprise, within ranges not impeding the effect of the invention, the following ingredients which should be properly used depending on the purpose; oily materials such as higher alcohols, higher fatty acid esters and the like; nonionic surface active agents which serve as an emulsifier or solubilizer include as polyoxyethylene lauryl ether, polyoxyethylene sorbitan monolaurylate, polyoxyethylene hardened castor oil and the like; wetting agents such as glycerine, propylene glycol and the like; and perfumes, colorants and the like.

The hair set lotions according to the present invention may be applied to the hair as they are or may be applied in the form of a mist by the use of a pump spray or the like means, or may be filled in a container together with a jetting agent such as freon gas, liquefied hydrocarbon, carbonic acid gas or the like, and applied in the form of a mist or foam.

The thus obtained hair set lotions can form a uniform tenacious film after drying and exhibit excellent hair setting strength even under high humidity conditions. Also, it can be readily removed from the hair when the hair is washed with a usually employed shampoo comprising anionic active agents and the like. Thus, the hair set lotion of the invention can satisfy both the requirements of setting performance and washability.

(4) First agent for permanent wave

In a first agent composition for permanent wave which comprises a substrate of reductive substance, essential ingredients used in the present invention are added thereby preparing the first liquid.

Reductive substances for use as a substrate of the first agent for permanent wave may be any conventionally employed substances, of which ammonium thioglycollate and cysteine hydrochloride are preferable.

The first agent for perm according to the invention is prepared by mixing the above ingredients by a method known per se. Aside from the above-mentioned ingredients, other known ingredients used for this purpose may be added including colorants, perfumes, oils, opacifiers, water-soluble silicones, organic salts, urea and the like.

(5) Second agent for permanent wave

Essential ingredient or ingredients of the present invention are added to a second agent composition for permanent wave which comprises oxidative substances as a substrate thereby preparing the second agent.

The amount of an oxidative substrate in the second agent may vary depending on whether or not the agent is dissolved in solvents or the degree of dilution when the agent is used as diluted, and is generally in the range of 1–30%, preferably 3–20%.

Oxidative substances which are a substrate of the second agent for permanent wave may be any ordinarily employed substances including, for example, alkali metal bromates such as sodium bromate, potassium bromate and the like, hydrogen peroxide, sodium percarbonate, sodium perborate and the like. Of these, alkali metal bromates are most perferably used.

The second agent for perm according to the invention may further comprise, aside from the above-indicated essential ingredients, anionic surface active agents, amphoteric surface active agents, nonionic surface active agents, cationic surface active agents, cationic polymer compounds, water-soluble silicones, urea, suitable oils, humectants, perfumes, colorants and the like arbitrary materials. These ingredients should be used within ranges of amounts not impeding the effect of the invention.

Specific examples of the cationic polymer compounds include cationic cellulose derivatives, cationic starch, diallyl quaternary ammonium salts or copolymers of diallyl quaternary ammonium salts and acrylamide, polyglycol polyamine condensate, methacryloxyethyltrimethylammonium salts, copolymers of methacryloxyethyltrimethylammonium salts and polyvinylpyrrolidone, and the like. Preferably, cationic cellulose derivatives which are available typically under the commercial name of "Polymer JR", diallyl quaternary ammonium salts available typically under the commercial name of "Merquat 100", and diallyl quaternary ammonium salt/acrylaimde copolymers typical of which is a product commercially available under the name of "merquat 550" can be mentioned. The amount of the cationic polymer compounds is preferably in the range of 0.01–5% and most preferably 0.05–2%.

The thus obtained second agent is so controlled that its 5% aqueous solution has a pH below 9, preferably 3.5–6.5.

(6) Hair Dye

A hair dye is prepared by admixing essential ingredients of the present invention with a hair dye substrate in a usual manner.

Flavanol derivatives are soluble in water and can be added as they are.

Any hair dye substrates ordinarily employed are usable in the practice of the invention. Examples of oxidation hair dyes and transient hair dyes can be mentioned as follows.

(i) Oxidation hair dyes

Dye intermediates, oxidents and, if necessary, couplers or modifiers are mixed together.

Examples of dye intermediates include p- and o-compounds such as p-phenylenediamine, toluene-2,5-diamine, N-phenyl-p-phenylenediamine, 4,4'-diaminodiphenylamine, p-aminophenol, p-methylaminophenol, o-phenylenediamine, toluene-3,4-diamine, o-aminophenol, p-chloro-o-phenylenediamine, p-amino-o-cresol, o-chloro-p-phenylenediamine, phloroglucin, phrogallol, 3,3'-iminodiphenyl, diphenylamine, 2,6-diaminopyridine, p-aminophenylsulfamine and the like.

Couplers or modifiers include meta compounds and phenols such as m-phenylenediamine, toluene-2,4-diamine, p-methoxy-m-phenylenediamine, m-aminophenol, α-naphthol, resorcin, hydroquinone, catechol and the like.

As an oxidant, hydrogen peroxide is usually used, but other oxidants may also be used including sodium perborate, urea peroxide, sodium percarbonate, sodium pertripolyphosphate, sodium pyrophosphate, sodium perorthophosphate, sodium silicatehydrogen peroxide addition product, sodium sulfate-sodium chloride-hydrogen peroxide addition product and the like.

Direct dyes and particularly nitro dyes which do not take part in the color formation reaction but give an influence on hair color may be used.

Examples of such dyes include nitro-p-phenylenediamine, p-nitro-o-phenylenediamine, 2-amino-4-nitrophenol, 2-amino-5-nitrophenol, 4-amino-2-nitrophenol and the like. If necessary, picramic acid, picric acid, and 1,4-diaminoanthraquinone may be added.

Within ranges of amounts not impeding the effect of the invention, there may be further added nonionic surface active agents, cationic surface active agents, solvents such as propylene glycol, glycerine and the like; lower alcohols such as ethyl alcohol, isopropyl alcohol and the like; viscosity adjusters such as hydroxyethyl cellulose, methyl cellulose, cationic polymer compounds, higher alcohols and the like; humectants, protein denaturing agents such as urea, perfumes, colorants, UV absorbers, antioxidants, preservatives, pearling agents, lotionizing agents and the like.

Oxidation hair dyes of the invention are obtained by mixing the above-mentioned ingredients and essential ingredients according to the usual practice. These dyes are formed as a powder or cream-like preparation, and may be used as a single composition which is added to a shampoo substrate upon application. Alternatively, oxidation dyes and oxidants may be provided separately and one or both of the dyes and oxidants are admixed with the essential ingredients to give powder, cream or liquid preparations. Upon application, both the preparations are mixed together.

(ii) Transient hair dyes

Dyestuffs and pigments are not critically limited with respect to their types. For instance, there are used pigments such as titanium oxide, carbon black and the like; and tar colorants such as triphenylmethane dyes, azo dyes, guinoline dyes, xanthene dyes, acridine dyes, azine dyes, oxazine dyes, indigoid dyes, anthraquinone dyes, stilbene dyes, thiazole dyes and the like.

Usable resins include, for example, copolymers of acrylates and methacrylates, copolymers of monochloroacetic acid.amine salt modified product of N,N'-dimethylaminoethyl methacrylate and methacrylates, copolymers of vinyl pyrrolidone and vinyl acetate, and the like.

Transient hair dyes are prepared by dissolving or dispersing the essential ingredients, and resins, dyes and pigments in dispersion media such as water, amyl alcohol, isopropanol, ethanol, acetone and the like. Further, other constituent ingredients ordinarily used for transient hair dyes may be added, if necessary, and examples of such ingredients include anionic surface active agents, cationic surface active agents, amphoteric surface active agents, nonionic surface active agents, polyhydric alcohols such as propylene glycol, glycerine, polyethylene glycol and the like; higher alcohols such as isostearyl alcohol, oleyl alcohol and the like; fatty acids such as lanolin fatty acids, coconut oil fatty acids and the like; esters such as isopropyl myristate; hydrocarbons such as liquid paraffin, cationic polymer compounds, amines, perfumes and the like.

(7) Pre-shampoo treatments

Pre-shampoo treatments are prepared by dissolving or suspending the afore-indicated essential ingredients and known ingredients added as required in a suitable medium such as water.

The known ingredients include fats and oils such as higher alcohols, fatty acid esters and the like; nonionic surface active agents serving as an emulsifier and solubilizer such as polyoxyalkylene alkyl ethers; and wetting agents such as glycerine, pyrrolidonecarboxylic acids and the like. By the addition of these ingredients, touch of the hair which has been treated with a pre-shampoo of the invention and washed with water can arbitrarily be controlled. For instance, when liquid oil ingredients are added, softness can be imparted to the hair. Addition of wetting agents results in a softer and wetter touch. Higher alcohols can impart smoothness to the hair.

The present invention is described by way of examples, which should not be construed as limiting the invention thereto.

EXAMPLE 1

Shampoo

Shampoo compositions having formulations indicated in Table 1-A were prepared and subjected to a performance evaluation test. The test results are shown in Table 1-B.

In examples, performances were evaluated as follows.

(1) Lathering Test

To an aqueous solution of 1% shampoo composition was added 0.1% of lanolin as an artificial stain, followed by stirring in a cylinder for 5 minutes at 40° C. using a flat propeller at 1000 rpm under conditions that the propeller was turned in reverse every 10 seconds. 30 seconds after completion of the stirring, an amount of the lather was measured for evaluation.

(2) Touch of Lather 30 g of human hairs was wetted with water of 40° C. to have 20 g of water contained therein. Subsequently, 1 g of a shampoo composition was used for hair washing and touch of the lather was organoleptically judged by 20 female panelists.

Evaluation Item

The degree of finger passage through hairs on washing was evaluated as "lather smoothness".

○ Better in lather smoothness than a reference shampoo.

Δ Slightly better than a reference shampoo.

× Equal to a reference shampoo.

(3) Combing Strength 30 g of human hairs were wet with water of 40° C. to have 20 g of water contained therein. 1 g of a shampoo composition was used for hair washing, followed by rinsing two times. After squeezing, the hairs were set in strain gauge and applied with a comb to measure a force exerted on the comb (wet condition). Then, the hairs were dried with a dryer and allowed to stand in an air-conditioned room of 20° C. and 65% R.H. overnight. Thereafter, the hairs were set in a strain gauge, and applied with a comb to measure a force exerted on the comb (dry condition).

(4) Hair Fly

Upon measurement of "combing force" under dry conditions, it was visually observed whether or not a hair fly phenomenon electrostatically took place.

× Hair Fly occurred

○ No hair fly occurred.

TABLE 1-A

|  | A | B | C |
| --- | --- | --- | --- |
| Sodium polyoxyethylene(2) laurylsulfate | 15% | 15% | 15% |
| Coconut fatty acid diethanolamide | 3 | 3 | 3 |
| Extract from green tea* | — | 0.5 | 0.5 |
| Hydrolyzate of silk (average molecular weight of 20,000) | — | — | 0.1 |
| Perfume | Suitable amount | Suitable amount | Suitable amount |
| Water | Balance | Balance | Balance |

TABLE 1-A-continued

|  | A | B | C |
| --- | --- | --- | --- |
|  | (pH 7.2) | (pH 7.2) | (pH 7.2) |

*Green tea extract
10 parts of water was added to 1 part of commercially available coarse tea leaves, followed by extraction at 90° C. for 1 hour. Thereafter, the solid matter was removed by filtration to obtain an aqueous extract. This extract contained 0.2% of flavanol derivatives such as catechin, epigallocatechin, epigallocatechin gallate and the like.

TABLE 1-B

|  | Lather Characteristics | | Styling of Hairs | |
| --- | --- | --- | --- | --- |
|  | Lathering | Lather Smoothness | Combing Force (g) | Hair fly |
| A | 114 | × | 210 | × |
| B (Product of Invention) | 165 | ○ | 100 | ○ |
| C (Product of Invention) | 172 | ○ | 90 | ○ |

EXAMPLE 2

Hair Rinse

Hair rinses of the compositions indicated in Table 2 were prepared. 500 ml of a 1:50 dilution of each hair rinse was used to treat the hair, followed by rinsing with hot water two times and air drying. The respective compositions were evaluated by the 5 grades method by 20 panelists. The evaluation standard was as follows: good (5), fair (4), moderate (3), rather poor (2) and poor (1). The results are shown in Table 3 in terms of average values.

TABLE 2

|  | D | E | F | G |
| --- | --- | --- | --- | --- |
| Distearyldimethylammonium chloride | 2% | 2% | 2% | 2% |
| Stearyl alcohol | 1% | 1% | 1% | 1% |
| Green tea extract* | — | 1% | — | 1% |
| Hydrolyzate of silk (average molecular weight 20,000) | — | — | 1% | 1% |
| Water | Balance (pH 5.0) | Balance (pH 5.0) | Balance (pH 5.0) | Balance (pH 5.0) |

TABLE 3

|  | Softness | Smoothness | Ease in Combing |
| --- | --- | --- | --- |
| D | 1.2 | 1.3 | 1.2 |
| E (Product of Invention) | 4.1 | 4.2 | 3.9 |
| F | 3.2 | 3.4 | 2.5 |
| G (Product of Invention) | 4.3 | 4.5 | 4.2 |

EXAMPLE 3

Hair Treatment

Hair treatments (H)-(K) based on the following fundamental formulation were prepared.

(Fundamental formulation)

Liquid paraffin: 5.0%
White vaseline: 2.0%
Cetyl alcohol: 2.0%
POE(20)sorbitan monostearate: 1.0%
Glycerine: 10.0%
Water: Balance
pH 7.0

To the above formulation:

(H) No materials added;

(I) 1.0% of a green tea extract added;

(J) 2.0% of a silk hydrolyzate (average molecular weight 20,000) added; and (K) 1.0% of a green tea extract and 2.0% of a silk hydrolyzate added.

These hair treatments were subjected to the following evaluations according to the five grades method. Average values of these evaluations are shown in Table 4.

TABLE 4

|   | Organoleptic Evaluation | Combing Force (g) Wet Condition | Combing Force (g) Dry Condition |
| --- | --- | --- | --- |
| H | 2.1 | 420 | 360 |
| I (Treatment of Invention) | 3.8 | 140 | 120 |
| J | 2.6 | 310 | 270 |
| K (Treatment of Invention) | 4.6 | 120 | 110 |

EXAMPLE 4

Hair Set Lotion

Hair set lotions of the formulations indicated in Table 5 were prepared to determine set retentivity thereof. The results are shown in Table 6.

Formulations:

TABLE 5

|   | L | M | N |
| --- | --- | --- | --- |
| Ethanol | 10% | 10% | 10% |
| Green tea extract | — | 2.0% | 2.0% |
| Hydrolyzate of collagen (average molecular weight 2,000) | — | — | 1.0% |
| Polyoxyethylene oleyl ether (EO20) | 0.5% | 0.5% | 0.5% |
| Perfume | 0.1% | 0.1% | 0.1% |
| Water | Balance | Balance | Balance |

$$\text{Set retentivity (\%)} = \frac{Lo - Lt}{Lo - Ls} \times 100$$

Lo = 14 (cm)

Ls = Length of a curl immediately after suspending at 95% R.H. (cm).

Lt = Length of a curl 30 minutes after suspending at 95% R.H. (cm).

TABLE 6

|   | Set Retentivity |
| --- | --- |
| L | 53% |
| M (Set Lotion of Invention) | 79% |
| N (Set Lotion of Invention) | 83% |

EXAMPLE 5

Blow Styling Lotion

Blow styling lotions of the formulations indicated in Table 7 were prepared and evaluated by an evaluation panel consisting of 18–35 years old female panelists to determine set retentivity, feeling of styled hair and feeling after hair washing by Scheffe's paired comparison. The test results are shown in Table 8.

Formulations:

TABLE 7

|   | O | P | Q |
| --- | --- | --- | --- |
| Ethanol | 10% | 10% | 10% |
| Polyoxyethylene oleyl ether (20EO) | 0.5% | 0.5% | 0.5% |
| Perfume | 0.1% | 0.1% | 0.1% |
| Green tea extract | — | 1.0% | 1.0% |
| α-keratose (average molecular weight 20,000) | — | — | 0.5% |
| Water | Balance | Balance | Balance |

TABLE 8

|   | Set Retentivity | Feeling of Styled Hair | Feeling after Hair Washing |
| --- | --- | --- | --- |
| Inventive lotion P is better | 11 | 12 | 20 |
| P is slightly better | 16 | 15 | 8 |
| No great difference is present | 2 | 2 | 2 |
| O is slightly better | 1 | 1 | 0 |
| O is better | 0 | 0 | 0 |
| Inventive lotion Q is better | 15 | 16 | 22 |
| Q is slightly better | 13 | 11 | 7 |
| No great difference is present | 1 | 2 | 1 |
| O is slightly better | 1 | 1 | 0 |
| O is better | 0 | 0 | 0 |

EXAMPLE 6

First Agent of Permanent Wave

Perm was effected using first and second agents for permanent wave indicated in Table 9 to determine waving, wave retentivity, adsorptivity and texture of the hair. The results are shown in Table 10.

Formulations:

(1) Permanent wave first agent:

TABLE 9

|   | R | S-1 | T-1 | S-2 | T-2 |
| --- | --- | --- | --- | --- | --- |
| Ammonium thioglycollate | 7% | 7% | 7% | 7% | 7% |
| Green tea extract | — | 1% | 1% | — | — |
| Roasted green tea extract* | — | — | — | 1% | 1% |
| Silk hydrolyzate (Average molecular weight 1,500) | — | — | 2% | — | 2% |
| Water (aqueous ammoniacal solution for pH adjustment) | 93% | 92% | 90% | 92% | 90% |

*Roasted green tea extract
1 part of commercially available roasted green tea (Hoojicha) leaves was admixed with 10 parts by weight of water, followed by extraction at temperatures over 90° C. for about 1 hour. The solid matter was cetrigugally separated and the filtrate was used.

(2) Permanent wave second agent:

Sodium bromate: 5.0%

Water: 95.0%

Test Methods:

(1) Measurements of Waving and Wave Retentivity (i) 20 hairs were bundled and the bundle was fixedly secured to cylinders of a wave measuring plate (on which two arrays of thin cylinders, each having a diameter of 2 mm and a length of 1.5 cm, were set in a zigzag form). This plate was immersed in a first agent of each of formulations 1–4 at 30° C. for 10 minutes and then in the second liquid agent at 30° C. for 10 minutes. After sufficiently rinsing with water, the bundle was removed from the measuring plate. A waving was calculated in stationary water according to the following equation.

It will be noted that the hairs used were 20 cm long virgin hairs which was washed with an aqueous 0.5% sodium laurylsulfate and dried.

$$\text{Waving (\%)} = \frac{X - Z}{X - Y} \times 100$$

X: Length of hairs fixed between distant points A and B of one array of the zigzag cylinders.
Y: Distance between A and B.
Z: Distance between points of the hairs, once contacted with points A and B, in stationary water after removal from the measuring plate.

(ii) The hair bundle used in (i) was gently moved while immersing in an aqueous 0.5% sodium laurylsulfate solution for 1 minute, rinsed sufficiently and dried in air over one day. The above procedure was repeated 4 times and after washing at the fifth washing, value Z was measured in stationary water to determine a waving value. This value was compared with a waving value prior to hair washing to give a wave retentivity according to the following equation.

$$\text{Wave Retentivity (\%)} = \frac{\text{Waving after Fifth Washing}}{\text{Waving before Washing}} \times 100$$

(2) Adsorptivity

The hair bundle used for the measurement of waving was observed under scanning electronic microscope to check the presence or absence of adsorbate of hair surfaces. The degree of adsorption was evaluated in ranks. The evaluation standard is shown below.

| Degree of Adsorption | Surface State of Hair |
| --- | --- |
| ++ | Smoothly covered with film. |
| + | Slight adsorbate is observed with smooth appearance. |
| − | Flaking of cuticle is observed with considerable irregularities. |

(2) Evaluation of Touch

Hair bundles consisting of Japanese virgin hairs were immersed in first agents R to T-2 at 30° C. for 10 minutes and then in the second agent at 30° C. for 10 minutes. After rinsing sufficiently with water, air-dried hair bundles were evaluated in five ranks by 20 female panelists. The evaluation standard is as follows: good (5), slightly good (4), moderate (3), slightly bad (2), and bad (1). The results are expressed in terms of geometric average.

Results:

TABLE 10

| Permanent Wave First Agent | Adsorptivity | Waving (%) | Wave Retentivity (%) | Evaluation of Touch |
| --- | --- | --- | --- | --- |
| R | − | 52 | 73 | 2.4 |
| S-1 (Inventive Agent) | + | 56 | 87 | 3.5 |
| T-1 (Inventive Agent) | ++ | 58 | 89 | 3.8 |
| S-2 (Inventive Agent) | + | 55 | 84 | 3.0 |
| T-2 (Inventive Agent) | ++ | 59 | 86 | 3.3 |

EXAMPLE 7

Permanent Wave Second Agent

Permanent wave was effected using a first agent of the following formulation and second agents of formulations indicated in Table 11. The degree of imparing of hairs experienced during the treatment was determined by measuring a variation in weight of the hairs prior to and after the treatment. The measurement of the weight of the hairs and the evaluation standard are described below.

[Formulation]
(First Agent)
Thioglycollic acid: 7.0%
Polyoxyethylene hardened caster oil: 1.0%
Perfume: 0.2
Ammoniacal solution, water: Balance
(pH was adjusted to 9.0 using ammoniacal solution.)

TABLE 11

| | (Second Agent) | | |
| --- | --- | --- | --- |
| | U | V | W |
| Sodium bromate | 5% | 5% | 5% |
| Amphoteric surface active agent ("Miranol CSM-SF" by Miranol Co., Ltd.) | 0.5% | 0.5% | 0.5% |
| Perfume | 0.1% | 0.1% | 0.1% |
| Green tea extract | — | 1.0% | 1.0% |
| Silk hydrolyzate (average molecular weight of 1500) | — | — | 2.0% |
| Water | Balance | Balance | Balance |

(Measurement of Weight of Hairs)

10 cm long virgin hairs were washed with an aqueous 0.5% sodium laurylsulfate solution and air-dried to provide them as hairs to be tested. About 1 g of the hairs were bundled and placed in a desiccator using a phosphorus pentaoxide dryer, followed by drying under reduced pressure over 1 week. Then, the weight of the dried hair bundle was measured and determined as a bone dry weight. The hair bundle was immersed in the first agent at 30° C. for 10 minutes, washed sufficiently with water and immersed in each of the second agents at 30° C. for 10 minutes. After sufficient washing with water, the bundle was air-dried and again dried in the same manner as described above, followed by measuring the weight of the permed bundle to give its bone dry weight.

| Evaluation | (Evaluation Standard) Contents |
| --- | --- |
| ◎ | The difference in bone dry weight between the virgin hair bundle and the permed hair bundle is less than 1%. |
| ○ | The difference in bone dry weight between the virgin hair bundle and the permed hair bundle is larger than 1% but less than 5%. |
| X | The difference in bone dry weight between the virgin hair bundle and the permed hair bundle is larger than 5%. |

Results
U: X
V (Inventive Product): ○
W (Inventive Product): ◎

EXAMPLE 8

Hair Dyes

Two-component hair dye compositions of the formulations indicated in Table 12 were prepared. An influence of each composition on the hair was evaluated by measuring weights of the hair before and after the dyeing treatment. The results are shown below.

Compositions:

TABLE 12

| (First Liquid) | | | | | |
|---|---|---|---|---|---|
|  | X | Y-1 | Z-1 | Y-2 | Z-2 |
| p-Phenylendiamine | 1.0% | 1.0% | 1.0% | 1.0% | 1.0% |
| Green tea extract | — | 1.0% | 1.0% | — | — |
| Black tea extract* | — | — | — | 1.0% | 1.0% |
| Silk hydrolyzate (average molecular weight 20,000) | — | — | 0.5% | — | 0.5% |
| Propylene glycol | 10.0% | 10.0% | 10.0% | 10.0% | 10.0% |
| Disodium EDTA | 0.3% | 0.3% | 0.3% | 0.3% | 0.3% |
| Sodium sulfite | 0.5% | 0.5% | 0.5% | 0.5% | 0.5% |
| Perfume | 0.1% | 0.1% | 0.1% | 0.1% | 0.1% |
| Water | Balance | Balance | Balance | Balance | Balance |

| (Second Liquid) | |
|---|---|
| Hydrogen peroxide | 6.0% |
| Water | 94.0% |

*Black tea extract
1 part of commercially available black tea leaves was admixed with 10 parts by weight of water, followed by extraction at temperatures over 90° C. for about 1 hour. The solid matter was separated by centrifugation and the filtrate was used. (pH was adjusted to 10.0 by the use of ammoniacal solution.)

Evaluation Method:

10 cm long virgin hairs were washed with an aqueous 0.5% sodium laurylsulfate solution and air-dried to give hairs to be tested. About 1 g of the hairs was bundled and placed in a desiccator using phosphorus pentaoxide as a dryer, followed by drying under reduced pressure over 1 week. The dried bundle was measured to give a bone dry weight of the virgin hairs.

Thereafter, the hairs being tested were subjected to a dyeing treatment and air-dried, followed by drying and measuring in the same manner as described above to give a bone dry weight of the treated hair bundle.

The weight of the hair bundle after the hair dyeing treatment was compared with the virgin hair bundle and evaluated according to the following evaluation standard. An influence of the dye compositions on the hair was judged based on the evaluation.

| Evaluation | (Evaluation Standard) Contents |
|---|---|
|  | Increasing over the hair weight prior to the treatment. |
|  | Decreasing by 0–3% as compared with the hair weight prior to the treatment. |
| X | Decreasing by over 3% as compared with the hair weight prior to the treatment. |

Hair Dyeing Method:

The first and second liquid agents were mixed in equal amounts to give a hair dye liquid, followed by diluting to a ratio of 1:5. The hair bundle was immersed in the solution at room temperature for 30 minutes and dyed. Subsequently, the dye was washed off using tap water of 40° C. and the bundle was washed with an aqueous 0.5% sodium laurylsulfate solution. Then, it was instantaneously immersed in an aqueous 1N acetic acid solution and again washed with tap water of 40° C.

Results
- x: ×
- Y-1 (Inventive Product): ○
- Z-1 (Inventive Product): ◎
- Y-2 (Inventive Product): ○
- Z-2 (Inventive Product): ◎

EXAMPLE 9

Hair Dye

Transient hair dye compositions (hair colorants) of the mascara type having the formulations indicated in Table 13 were prepared. 0.5 g of each of the compositions was applied onto 1 g of grey hairs. After air drying, the applied hairs were organoleptically evaluated by 10 expert panels with respect to gloss, smoothness and favorite in touch. The results are shown in Table 14.

Compositions:

TABLE 13

|  | A′ | B′-1 | C′-1 | B′-2 | C′-2 |
|---|---|---|---|---|---|
| Polymer resin* | 12.0% | 12.0% | 12.0% | 12.0% | 12.0% |
| Pigment (carbon black) | 1.0% | 1.0% | 1.0% | 1.0% | 1.0% |
| Green tea extract | — | 1.0% | 1.0% | — | — |
| Epicatechin | — | — | — | 0.005% | 0.005% |
| Silk hydrolyzate (average molecular weight 20,000) | — | — | 0.5% | — | 0.5% |
| Perfume | 0.1% | 0.1% | 0.1% | 0.1% | 0.1% |
| Ethanol | Balance | Balance | Balance | Balance | Balance |

*Polymer resin: Copolymer of monochloroacetic acid amine salt modified product of N,N′—dimethylaminoethyl methacrylate and methacrylic acid ester.

Results:

TABLE 14

|  | Evaluation Performances | | |
|---|---|---|---|
|  | Gloss | Smoothness | Touch |
| A′ | X | X | X |
| B′-1 (Product of Invention) | Δ | ○ | ○ |
| C′-1 (Product of Invention) | ○ | ○ | ○ |
| B′-2 (Product of Invention) | Δ | ○ | ○ |
| C′-2 (Product of Invention) | ○ | ○ | ○ |

(In the table, the marks in performances are as follows: indicated by "○" is good, by "Δ" is slightly good and by "X" is poor.)

EXAMPLE 10

Hair Liquid

Composition:

| (a) Green tea extract | 1.0% |
|---|---|
| (b) Silk hydrolyzate (average molecular weight 20,000) | 0.1% |
| (c) Polyoxypropylene (30 butyl ether) | 15.0% |
| (d) Ethanol | 40.0% |
| (e) Water | 44.0% |

Preparation:

(a)–(e) were mixed and completely dissolved together to obtain a hair liquid.

EXAMPLE 11

Hair Tonic

Composition:

| | |
|---|---|
| (a) Green tea extract | 1.0% |
| (b) Silk hydrolyzate (average molecular weight 20,000) | 0.1% |
| (c) PCA-Al | 0.5% |
| (d) Ethanol | 55.0% |
| (e) Water | 44.0% |

Preparation:

The above ingredients (a)–(e) were mixed while agitating until uniform solution was obtained.

EXAMPLE 12

Set Lotions

Set lotions of the formulations indicated in Table 15 were prepared and checked with respect to touch and set retentive effect of the hair applied therewith.

TABLE 15

| | D' | E' | F' |
|---|---|---|---|
| Catechin | — | 0.005% | 0.005% |
| Silk hydrolyzate (MW 20,000) | — | — | 0.2% |
| Cationic polymer (Polymer JR 400) | 1.0 | 1.0 | 1.0 |
| Sodium chloride | 1.0 | 1.0 | 1.0 |
| Ethanol | 5.0 | 5.0 | 5.0 |
| Water | Balance | Balance | Balance |
| pH | (7.0) | (7.0) | (7.0) |

Test Methods:

(1) Touch of Treated Hairs

A bundle of Japanese female hairs having a length of 30 cm and a weight of 20 g was applied with a hair cosmetic and spread sufficiently over the bundle and rinsed with running water of 40° C. for 1 minute, after which the bundle was organoleptically evaluated. The organoleptic evaluation was made by Scheffe's paired comparison in which a hair bundle treated with a commercially available hair rinse comprising major proportions of a quaternary ammonium salt and a hydrocarbon was used as reference. (In Table, an average value of 20 expert panels is shown.)

| Evaluation Point | Evaluation |
|---|---|
| +2 | Better in touch than the reference hair bundle. |
| +1 | Slightly better than the reference hair bundle. |
| 0 | Equal in touch to the reference hair bundle. |
| −1 | Slightly poorer in touch than the reference hair bundle. |
| −2 | Poorer than the reference hair bundle. |

(2) Set Retentive Effect 5 g of a bundle of Japanese female hairs having a length of 20 cm and a weight of 5 g was applied with 1 g of a hair cosmetic and spread over the bundle, followed by rinsing with running water of 40° C. for 1 minute. Additional water was removed by filter paper and the bundle was wound around a glass tube with a diameter of 1.5 cm such that a winding width was 5 cm, with opposite ends being secured. The thus wound bundle was allowed to stand under conditions of 65% R.H. and 20° C. for 24 hours, by which it was curled. After 24 hours, the bundle was removed and vertically suspended to measure its length. The degree of curling was calculated according to the following equation.

$$\text{Degree of curling (\%)} = \frac{A - (B - A)}{A} \times 100$$

A: Length of the hair immediately after removal from the glass tube.

B: Length of the hair 12 hours after removal from the glass tube.

(3) Measurement of Combing Force in Wet Condition

After evaluation of the touch of the hair bundle, the bundle was set on a strain gauge, followed by combing with a nylon comb 20 times to record resistance forces. An average value of the forces was given as a combing force.

(4) Measurement of Touch and Combing Force in Dry Condition

After the measurement of the touch and combing force in wet condition, the hair bundle was air-dried and evaluated according to the methods (1) and (3).

Results:

татабLE 16

| | Touch of Hair | Degree of Curling | Combing Force | |
|---|---|---|---|---|
| | | | Wet | Dry |
| D' | −0.1 | 72% | 170 (g) | 194 (g) |
| E' | +1.7 | 92% | 195 | 201 |
| F' | +1.9 | 95% | 230 | 213 |

Reference

Preparation of Green Tea Extract:

10 parts of water was added to 1 part of commercially available coarse tea leaves, followed by extraction at 90° C. for 1 hour. Thereafter, the solid matter was removed by filtration to obtain an aqueous extract. This extract contained 0.2% of flavanol derivatives such as catechin, epigallocatechin, epigallocatechin gallate and the like

What is claimed is:

1. A hair cosmetic, comprising:
   (a) at least one flavanol derivative selected from the group consisting of epicatechin, epigallocatechin, epicatechin gallate, epigallocatechin gallate, catechin, and gallocatechin; and
   (b) at least one peptide compound selected from the group consisting of collagen, keratin and silk.

2. The hair cosmetic of claim 1, wherein said peptide compound is silk.

3. The hair cosmetic of claim 1, wherein said peptide compound is keratin.

4. The hair cosmetic of claim 1, wherein the amount of flavanol derivative in said hair cosmetic ranges from 0.0001 wt. % to 1 wt. %.

5. The hair cosmetic of claim 4, wherein the amount of said flavanol derivative ranges from 0.0005–0.1 wt. %.

6. The hair cosmetic of claim 5, wherein the amount of said flavanol derivative ranges from 0.001–0.05% by weight.

7. The hair cosmetic of claim 1, wherein the amount of said peptide compound ranges from 0.01–10 wt. %.

8. The hair cosmetic of claim 7, wherein the amount of said peptide compound ranges from 0.05–3 wt. %.

9. The hair cosmetic of claim 1, wherein said hair cosmetic is a shampoo, hair rinse, after shampoo, conditioner, hair conditioner, set lotion, blow styling lotion, hair spray, hair dye, bleach, permanent wave first agent, permanent wave second agent, hair liquid or hair tonic.

10. A method of cosmetically treating the hair, comprising:
    treating said hair with a hair cosmetic formulation containing at least one flavanol derivative selected from the group consisting of epicatechin, epigallocatechin, epicatechin gallate, epigallocatechin gallate, catechin, and gallocatechin; and
    at least one peptide compound selected from the group consisting of collagen, keratin and silk.

* * * * *